United States Patent [19]

Edwardson et al.

[11] Patent Number: 5,770,194

[45] Date of Patent: *Jun. 23, 1998

[54] FIBRIN SEALANT COMPOSITIONS AND METHODS FOR UTILIZING SAME

[75] Inventors: Peter A. D. Edwardson, Chester; John E. Fairbrother; Ronald S. Gardner, both of Clwyd; Derek A. Hollingsbee, South Wirral; Stewart A. Cederholm-Williams, Oxford, all of United Kingdom

[73] Assignee: Bristol-Myers Squibb Company, Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 450,829

[22] Filed: May 25, 1995

Related U.S. Application Data

[60] Division of Ser. No. 138,674, Oct. 18, 1993, which is a continuation-in-part of Ser. No. 958,212, Oct. 8, 1992, abandoned.

[51] Int. Cl.⁶ .................................................. A61K 38/48
[52] U.S. Cl. ...................... 424/94.64; 424/529; 424/530; 530/382; 514/2; 514/21
[58] Field of Search .................................... 424/529, 530, 424/94.64; 530/383; 514/2, 21

[56] References Cited

U.S. PATENT DOCUMENTS

| | | | |
|---|---|---|---|
| 2,533,004 | 12/1950 | Ferry et al. | 260/112 |
| 3,849,252 | 11/1974 | Percs et al. | 195/62 |
| 3,933,996 | 1/1976 | Charlton et al. | 424/1 |
| 4,377,572 | 3/1983 | Schwartz et al. | 424/101 |
| 4,427,650 | 1/1984 | Stroetmann | 424/46 |
| 4,427,651 | 1/1984 | Stroetmann | 424/46 |
| 4,438,198 | 3/1984 | Schmer | 435/178 |
| 4,442,655 | 4/1984 | Stroetmann | 53/428 |
| 4,627,879 | 12/1986 | Rose | 106/124 |
| 4,709,037 | 11/1987 | Sigler | 546/271 |
| 4,714,457 | 12/1987 | Alterbaum | 494/37 |
| 4,909,251 | 3/1990 | Seelich | 606/213 |
| 4,915,847 | 4/1990 | Dillon et al. | 210/737 |
| 4,928,603 | 5/1990 | Rose et al. | 106/124 |
| 4,957,903 | 9/1990 | Ranby | 514/18 |
| 4,960,757 | 10/1990 | Kumpe et al. | 514/21 |
| 5,026,785 | 6/1991 | Mage et al. | 529/329.4 |
| 5,030,215 | 7/1991 | Morse et al. | 604/410 |
| 5,175,087 | 12/1992 | Ranby et al. | 435/13 |
| 5,180,828 | 1/1993 | Ghazarossian et al. | 546/37 |
| 5,185,001 | 2/1993 | Galanakis | 604/5 |
| 5,206,023 | 4/1993 | Hunziker | 424/423 |
| 5,252,743 | 10/1993 | Barrett et al. | 548/303.7 |
| 5,290,552 | 3/1994 | Sierra et al. | 424/94.64 |
| 5,330,974 | 7/1994 | Pines et al. | 514/21 |
| 5,405,607 | 4/1995 | Epstein | 424/94.64 |
| 5,420,250 | 5/1995 | Lontz | 530/381 |
| 5,510,102 | 4/1996 | Cochrum | 424/78.08 |
| 5,520,885 | 5/1996 | Coelho et al. | 422/101 |

FOREIGN PATENT DOCUMENTS

| | | |
|---|---|---|
| 0 068 149 A2 | 1/1983 | European Pat. Off. . |
| 0 423 938 A1 | 4/1991 | European Pat. Off. . |
| 0 423 938 B1 | 4/1991 | European Pat. Off. . |
| 0 472 205 A1 | 2/1992 | European Pat. Off. . |
| 0 534 178 A2 | 3/1993 | European Pat. Off. . |
| 129224 | 5/1990 | Japan . |
| WO-A-86 01814 | 3/1986 | WIPO . |
| WO-A-88 02259 | 4/1988 | WIPO . |
| WO-A-90 04786 | 5/1990 | WIPO . |
| WO-A-91 09573 | 7/1991 | WIPO . |
| WO-A-91 09641 | 7/1991 | WIPO . |
| WO-A-92 15341 | 9/1992 | WIPO . |
| WO-A-93 19805 | 10/1993 | WIPO . |

OTHER PUBLICATIONS

Yanagita et al., Chap. 3, "Solubilization and Purification of Membrane Proteins," in *Techniques for the Analysis of Membrane Proteins,* Ragan & Cherry (eds.) 1986.

Brennan, M., 1991, "Fibrin Glue", Blood Reviews 5:240–244.

Gibble et al., 1990, "Fibrin Glue—The Perfect Operative Sealant?", Transfusion 30:741–747. #8.

Matras, H., 1985, "Fibrin Seal—The State of the Art", J. Oral Maxillofac. Surg. 43:605–611.

Sierra, D., 1993, "Fibrin Sealant Adhesive Systems: A Review of Their Chemistry, Material Properties and Clinical Applications", J. Biomaterials Appl. 7:309–352. Apr.

Schlag et al., "Fibrin Sealant: Efficacy, Quality, and Safety" in *Progress in Fibrin Sealing,* Waclawiczek (ed.) 1989.

Lerner et al., 1990, "Current Status of Surgical Adhesives", J. Surg. Research 48:165–181.

Thompson et al., 1988, "Fibrin Glue: A Review of Its Preparation, Efficacy, and Adverse Effects as a Topical Hemostat", Drug Intell. Clin. Pharm. 22:946–952.

Jackson, C., 1980, "Blood Coagulation", Ann. Rev. Biochem. 49:765–811.

Furie et al., 1988, "The Molecular Basis of Blood Coagulation", Cell 53:505–518. May.

Doolittle, R., 1984, "Fibrinogen and Fibrin", Ann. Rev. Biochem. 53:195–229.

"Hemostasis and Blood Coagulation" in *Blood Cells, Immunity, and Blood Clotting,* Reed Reference Publishing 1994.

Ochsner et al., 1990, "Fibrin Glue as a Hemostatic Agent in Hepatic and Splenic Trauma", J. Trauma 30(7):884–887.

(List continued on next page.)

*Primary Examiner*—Chhaya D. Sayala
*Attorney, Agent, or Firm*—Theodore R. Furman, Jr.; John M. Kilcoyne

[57] ABSTRACT

The subject invention relates to fibrin sealants. More specifically, the subject invention relates to the use of a fibrin sealant wherein a composition comprising fibrin polymer is utilized as a component of the fibrin sealant.

2 Claims, No Drawings

OTHER PUBLICATIONS

Levinson et al., 1991, "Fibrin Glue for Partial Nephrectomy", Urology 38:314–316. Oct.

Dulchavsky et al., 1991, "Autologous Fibrin Gel: Bactericidal Properties in Contaminated Hepatic Injury", J. Trauma 31(7):991–995.

Epstein et al., 1986, "A New Autologous Fibrinogen–Based Adhesive for Otologic Surgery", Ann. Otol. Rhinol. Laryngol. 95:40–45.

Weisman et al., 1987, "Biochemical Characterization of Autologous Fibrinogen Adhesive", Laryngoscope 97:1186–1190. Oct.

Couto et al., 1987, "Autologous Fibrin Glue as a Sealant of the Common Bile Duct", Surgery 101:354–356.

Rupp, G., "Die Fibringeklebte Achillessehnenruptur" in *Fibrinkleber in Othopadie und Traumatologie*, ed. H. Cotta and A. Braun, Georg Thieme, Stuttgart, 1982, pp. 151–152.

Saltz et al., 1989, "Application of Autologous Fibrin Glue in Burn Wounds", J. Burn Care Rehabil. 10:504–507.

Chakravorty et al., 1989, "Autologous Fibrin Glue in Full–thickness Skin Grafting", Ann. Plast. Surg. 23:488–491. #6 Dec.

Mandel, M., 1989, "Autologous Fibrin for Blepharoplasty Incisions", JAMA 262:3271–3272. Dec. #23.

Rostron, C.K., 1989, "Epikeratophakia Grafts Glued with Autologous Cryoprecipitate", Eur. J. Implant. Refractive Surg. 1:105–108. Jun.

Weis–Fogh et al., 1990, "Autologous Fibrin Sealant in Reconstructive Rabbit Oviduct Microsurgery", Fertil. Steril. 54:157–160. #1 July.

Hartman et al., 1992, "Autologous Whole Plasma Fibrin Gel", Arch. Surg. 127:357–359. March.

Milde, L., 1989, "An Anaphylactic Reaction to Fibrin Glue," Anesth. Analg. 69:684–686.

Spotnitz et al., 1987, "Fibrin from Stored Human Plasma—An Inexpensive and Efficient Method for Local Blood Bank Preparation", Amer. Surg. 53(8):460–462.

Dresdale et al., 1985, "Hemostatic Effectiveness of Fibrin Glue Derived from Single–Donor Fresh Frozen Plasma", Ann. Thorac. Surg. 40(4):385–387. Oct.

Seelich, T., 1982, "Tissucol™ (Immuno, Vienna): Biochemistry and Methods of Application", J. Head & Neck Pathol. 3:65–69.

Mandel, M., 1990, "Closure of Blepharoplasty Incisions with Autologous Fibrin Glue", Arch. Ophthalmol. 108:842–844. Jun.

Sierra et al., 1990, "The Use of Fibrin Glue in Intracranial Procedures: Preliminary Results", Laryngoscope 100:360–363. Apr.

Arenberg et al., 1989, "Autologous Fibrin Glue and Sealant Standard and Microdrop Delivery Systems", Otolaryngol. Head and Neck Surg. 101(6):709–712.

Weis–Fogh, U., 1988, "Fibrinogen Prepared from Small Blood Samples for Autologous Use in a Tissue Adhesive System", Eur. Surg. Res. 20:381–389.

Tos et al., 1987, "How I Do It—Autologous Tissue Seal in Myringoplasty", Laryngoscope 97:370–371. Mar.

Durham et al., 1987, "A Method for Preparation of Fibrin Glue", J. Laryngol. and Otol. 101:1182–1186. Nov.

Laitakari et al., 1989, "Autologous and Homologous Fibrinogen Sealants: Adhesive Strength", Layngoscope 99:974–976. Sep.

Silberstein et al., 1988, "An Autologous fibrinogen–based Adhesive for Use in Otologic Surgery", Transfusion 28(4):319–321.

Feldman et al., 1988, "Compatibility of Autologous Fibrin Adhesive with Implant Materials", Arch. Otolaryngol. Head Neck Surg. 114:182–185. Feb.

Siedentop et al., 1985, "Autologous Fibrin Tissue Adhesive", Laryngoscope 95:1074–1076. Sep.

Seidentop et al., 1986, "Extended Experimental and Preliminary Surgical Findings with Autologous Fibrin Tissue Adhesive Made from Patient's Own Blood", Laryngoscope 96:1062–1064. Oct.

Alterbaum et al., 1985, "Autologous Fibrin Glue,(A New Method of Preparation)", Surg. Forum 36:544–546.

Moretz et al., 1986, "A Simple Autologous Fibrinogen Glue for Otoloic Surgery", Otolaryngol. Head Neck Surg. #1 95:122–124. June.

Gestring et al., 1983, "Autologous Fibrinogen for Tissue–adhesion Hemostasis and Embolization", Vasc. Surg. 17:294–304. Sep./Oct.

Wolf et al., 1984, "Re: The Concentrated Autologous Tissue Glue", Amer. J. Otol. 5(5):424–425. Jun.

Harris et al., 1987, "Autologous Fibrin Tissue Adhesive Biodegration and Systemic Effects", Laryngoscope 97:1141–1144. Oct.

Siedentop et al., 1988, "Autologous Fibrin Tissue Adhesive: Factors Influencing Bonding Power", Laryngoscope 98:731–733. July.

Marshall, S., 1978, "Commercial Fibrinogen, Autogenous Plasma, Whole Blood and Cryoprecipitate for Coagulum Pyelolithotomy: A Comparative Study", J. Urol. 119:310–311. Mar.

Gestring et al., 1981, "Hemostasis with Autologous Fibrinogen", Acta Chir. Austriaca 13:46–48.

Robbins, A Study on the Conversion of Fibrinogen to Fibrin, Am. J. Physiol. 142 (1944) pp. 581–88.

Hekma, Uber das Fibrin und seine Beziehung zu einigen Fragen der Biologie und Kolloidehemie, Inst. for Physiol. of Groningen Univ. (1914) pp. 311–331.

Stocker, Letter to the Editors–in–Chief/Reptilase–Test, Thrombosis Research 31; 765–766, 1983.

Blomback et al., A two–step fibrinogen–fibrin transition in blood coagulation, Nature 257, No. 5680, pp. 501–505 (Oct. 12, 1978).

Usero et al., Kinetic Analysis of the Fibrin Monomers Aggregation: Calculation of the Fibrinogen–Fibrin Equilibrium Constant, Int. J. Biochem vol. 12 pp. 1191–1196 (1981).

Wiltzius et al., Conformational Identity of Human Fibrinogen and Monomeric Fibrin, Thrombosis Research 19; pp. 793–798 (1980).

von Felten et al., Familial Disturbance of Fibrin Monomer Aggregation, Brit, J. Haemat., 1966, 12, pp. 667–677.

Lyapina et al., Method of Preparation of Fibrin Monomer, Council of Ministers, USSR, Bulletin No. 19, May 25, 1979.

Kjaergard et al., Vascular Surgery, vol. 27, pp. 249–252, 1993.

FIBRIN SEALANT COMPOSITIONS AND METHODS FOR UTILIZING SAME

This is a divisional application of U.S. Ser. No. 08/138,674 filed Oct. 18, 1993 which is a continuation-in-part application of U.S. Ser. No. 07/958,212 filed Oct. 8, 1992, now abandoned.

FIELD OF THE INVENTION

The subject invention relates to fibrin sealants. More specifically, the subject invention relates to the use of a fibrin sealant wherein a composition comprising fibrin monomer or a composition comprising noncrosslinked fibrin is utilized as a component of the fibrin sealant.

BACKGROUND OF THE INVENTION

One mechanism for hemostasis, i.e., prevention of blood loss, of a mammal is the formation of a blood clot. Clot formation in humans, i.e., blood coagulation, occurs by means of a complex cascade of reactions with the final steps being the conversion of fibrinogen—a monomer—by thrombin, calcium ions and activated factor XIII to form ultimately crosslinked fibrin II polymer, which is the fibrin clot.

The formation of crosslinked fibrin II polymer proceeds by the fibrinogen being converted by thrombin to fibrin I monomer, which spontaneously polymerizes to form fibrin I polymer, which is sometimes referred to as soluble fibrin I because by treatment by appropriate chemical means the fibrin I polymer can be reconverted to fibrin I monomer. The fibrin I polymer is then converted by thrombin to fibrin II polymer, which is sometimes referred to as soluble fibrin II because by treatment by appropriate chemical means the fibrin II polymer can be converted to fibrin II monomer. The fibrin II polymer, under the influence of factor XIIIa—known as activated factor XIII—is then crosslinked to form crosslinked fibrin II, which is the fibrin clot. Factor XIII is activated by thrombin in the presence of calcium ions. Cross-linked fibrin II is sometimes referred to as insoluble fibrin II because it cannot be converted to fibrin II monomer.

It should be noted that thrombin is formed from prothrombin. Prothrombin is converted to thrombin by factor Xa in the presence of calcium and other ancillary substances.

Fibrinogen represents about 2 to 4 grams/liter of the blood plasma protein. Fibrinogen is a monomer that consists of three pairs of disulfide-linked polypeptide chains designated $(A\alpha)_2$, $(B\beta)_2$, $\gamma_2$. "A" and "B" represent the two small aminoterminal peptides, known as fibrinopeptide A and fibrinopeptide B, respectively. The cleavage of fibrinopeptides A from fibrinogen in the transformation of fibrinogen by thrombin results in the fibrin I compound and the subsequent cleavage of fibrinopeptides B results in the fibrin II compound. Such cleavage of fibrinopeptides A and B reduces the molecular weight of fibrinogen by an extremely small amount, about 6,000 out of 340,000 daltons, but exposes the polymerization sites. For a review of the mechanisms of blood coagulation and the structure of fibrinogen, see C. M. Jackson, *Ann. Rev. Biochem.*, 49:765–811 (1980) and B. Furie and B. C. Furie, *Cell*, 53:505–518 (1988).

A fibrin sealant is a biological adhesive whose effect imitates the final stages of coagulation, thereby resulting in a fibrin clot. Conventional fibrin sealants consist of concentrated human fibrinogen, bovine aprotinin and factor XIII, as the first component and bovine thrombin and calcium chloride as the second component. Application is generally carried out with a double-barrelled syringe, which permits simultaneous application of both components to the site where one wants to form the fibrin clot. Aprotinin is a fibrinolytic inhibitor added to promote stability of fibrin sealants.

The fibrinogen component of the fibrin sealant is prepared from pooled human plasma. The fibrinogen can be concentrated from the human plasma by cryoprecipitation and precipitation using various reagents, e.g., polyethylene glycol, ether, ethanol, ammonium sulfate or glycine. For an excellent review of fibrin sealants, see M. Brennan, *Blood Reviews*, 5:240–244 (1991); J. W. Gibble and P. M. Ness, Transfusion, 30:741–747 (1990); H. Matras, *J. Oral Maxillofac Sura.*, 43:605–611 (1985) and R. Lerner and N. Binur, *J. of Surgical Research*, 48:165–181 (1990).

Recently, there has also been an interest in the preparation of fibrin sealants that utilize auto-logous fibrin. An autologous fibrin sealant is a fibrin sealant wherein the fibrinogen component of the fibrin sealant is extracted from the patient's own blood. The use of an autologous fibrin sealant is preferred because it eliminates the risk of transmission of blood-transmitted infections, e.g., hepatitis B, non A, non B hepatitis and acquired immune deficiency syndrome (AIDS), that could otherwise be present in the fibrinogen component extracted from pooled human plasma. See L. E. Silberstein et al., *Transfusion*, 28:319–321 (1988); K. Laitakari and J. Luotonen, *Laryngoscope*, 99:974–976 (1989) and A. Dresdale et al., *The Annals of Thoracic Surgery*, 40:385–387 (1985).

An infection can be transmitted by a fibrin sealant not only by means of the fibrinogen but also by means of the bovine aprotinin and the bovine thrombin component. Bovine thrombin has been known to carry the infectious agent bovine spongiform encephalitis (BSE) and other viruses pathogenic to mammals. Furthermore, bovine thrombin is a potent antigen, which can cause immunological reactions in humans. Thus, the use of bovine thrombin could result in the recipient of the bovine thrombin being adversely affected. See D. M. Taylor, *J. of Hospital Infection*, 18 (Supplement A) :141–146 (1991), S. B. Prusiner et al., *Cornell Vet*, 81 No. 2: 85–96 (1991) and D. Matthews, J. Roy. *Soc. Health*, 3–5 (February 1991).

Accordingly, there is the need for a fibrin sealant that can be delivered to a patient without the risk of viral contamination or other adverse affects.

SUMMARY OF THE INVENTION

The subject invention relates to a method for utilizing a fibrin sealant which comprises:

(a) contacting a desired site with a composition comprising fibrin monomer; and (b) converting said fibrin monomer to a fibrin polymer concurrently with said contacting step, thereby forming a fibrin clot.

The subject invention also provides methods for preparing such composition and compositions and kits comprising such fibrin monomer.

Another aspect of the subject invention relates to a method for utilizing a fibrin sealant which comprises:

(a) contacting a desired site with a composition comprising noncrosslinked fibrin; and (b) converting said noncrosslinked fibrin to crosslinked fibrin concurrently with said contacting step, thereby forming a fibrin clot.

The subject invention also provides methods for preparing such a composition and compositions and kits comprising such noncrosslinked fibrin.

DEFINITIONS

For the purpose of the subject invention, the following definitions are utilized:

Fibrin—Fibrin means any form of fibrin. Nonlimiting examples of fibrin include fibrin I, fibrin II and des BB fibrin. The fibrin can be in monomeric form or polymeric form, wherein the polymeric form is either noncrosslinked or crosslinked.

Fibrin Monomer—Fibrin monomer includes any form of fibrin, e.g., fibrin I, fibrin II or des BB fibrin, wherein the fibrin is in monomeric form or oligomeric form that can be solubilized in the composition comprising fibrin monomer and wherein the fibrin monomer can be converted to fibrin polymer.

Fibrin Polymer—Fibrin polymer includes any form of fibrin, e.g., fibrin I, fibrin II or des BB fibrin, wherein said fibrin is in polymeric form, either noncrosslinked or crosslinked.

Noncrosslinked Fibrin—Noncrosslinked fibrin includes any form of fibrin, e.g., fibrin I, fibrin II or des BB fibrin, wherein said fibrin is noncrosslinked and can be converted to crosslinked fibrin. The noncrosslinked fibrin can be fibrin monomer or noncrosslinked fibrin polymer.

Crosslinked Fibrin—Crosslinked fibrin includes any form of fibrin, e.g., fibrin I, fibrin II or des BB, wherein the fibrin is a fibrin polymer that is crosslinked.

DETAILED DESCRIPTION OF THE INVENTION

The subject invention relates to a method for utilizing a fibrin sealant which comprises:

(a) contacting a desired site with a composition comprising fibrin monomer; and (b) converting said fibrin monomer to a fibrin polymer concurrently with said contacting step, thereby forming a fibrin clot.

The subject invention also provides methods for preparing such composition and compositions and kits comprising such fibrin monomer.

Another aspect of the subject invention relates to a method for utilizing a fibrin sealant which comprises:

(a) contacting a desired site with a composition comprising noncrosslinked fibrin; and (b) converting said noncrosslinked fibrin to crosslinked fibrin concurrently with said contacting step, thereby forming a fibrin clot.

The subject invention also provides methods for preparing such composition and compositions and kits comprising such noncrosslinked fibrin.

THE COMPOSITION COMPRISING FIBRIN MONOMER

The fibrin composition of the subject invention comprising fibrin monomer is a composition that contains any form of fibrin monomer that can be converted to fibrin polymer. Nonlimiting examples of fibrin monomer include fibrin I monomer, fibrin II monomer or des BB fibrin monomer, with fibrin I monomer being preferred. Of course, mixtures of the fibrin monomer can be present. Also, for the purpose of the subject invention, fibrin polymer includes any polymer resulting from the polymerization of fibrin monomer. Thus, for example, the conversion of fibrin I monomer to fibrin polymer can result in fibrin I polymer, crosslinked or noncrosslinked, and/or fibrin II polymer, crosslinked or noncrosslinked, depending on how the conversion step is carried out.

Fibrin I monomer is preferred because it can, in contrast to fibrinogen, readily be converted to fibrin polymer without the use of thrombin or factor XIII. In fact, the fibrin I monomer can spontaneously form fibrin I polymer, which can act as the fibrin clot, regardless of whether the fibrin I polymer is crosslinked or noncrosslinked or further converted to fibrin II polymer. Thus, since the formation of the fibrin I polymer from fibrin I monomer is spontaneous, the fibrin I polymer can be formed without thrombin and factor XIII, thereby avoiding the problems associated with bovine thrombin. (It should be noted that if fibrin I monomer is utilized such that the fibrin I monomer comes into contact with patient's blood, for example, on a wound, the patient's thrombin and factor XIII may convert the fibrin I polymer to crosslinked fibrin II polymer.)

THE COMPOSITION COMPRISING NONCROSSLINKED FIBRIN

The composition comprising noncrosslinked fibrin is a composition that contains any form of noncrosslinked fibrin. Nonlimiting examples of noncrosslinked fibrin are noncrosslinked fibrin I, noncrosslinked fibrin II and des BB fibrin, with noncrosslinked fibrin I being preferred. Of course, mixtures of noncrosslinked fibrin can be present. Also, for the purpose of the subject invention "crosslinked fibrin" includes any form of fibrin resulting from the conversion of noncrosslinked fibrin to crosslinked fibrin. Thus, the crosslinked fibrin, for example, resulting from the conversion of noncrosslinked fibrin I to crosslinked fibrin, can be crosslinked fibrin I and/or crosslinked fibrin II, depending on how the conversion step is carried out.

Noncrosslinked fibrin I is preferred because it can more readily, as compared to fibrinogen, be converted to crosslinked fibrin. In fact, it is believed that fibrin I can form crosslinked fibrin I, which can act as the fibrin sealant. Thus, the formation of the crosslinked fibrin I from noncrosslinked fibrin I can be carried out without thrombin, thereby avoiding the problems associated with bovine thrombin, albeit activated factor XIII may be required. (It should be noted that if noncrosslinked fibrin I is utilized such that the noncrosslinked fibrin I comes into contact with patient's blood, for example, on a wound, the patient's thrombin and factor XIII may convert the fibrin I to crosslinked fibrin II.)

Also, the noncrosslinked fibrin can be a polymer, oligomer or monomer, albeit an oligomer or monomer is preferred, i.e., fibrin monomer. This is due to the fact that noncrosslinked fibrin in polymeric form is generally a gel and, therefore, is very difficult to deliver to the desired site and provides for less intimate contact with cells at the desired site. In contrast, a resulting noncrosslinked fibrin in oligomeric or monomeric form is soluble and, therefore, can more readily be delivered to the desired site and have more intimate contact with the cells. Of course, the composition can contain a mixture of such forms of noncrosslinked fibrin.

THE SOURCE OF THE COMPOSITION COMPRISING FIBRIN MONOMER OR NONCROSSLINKED FIBRIN

The source of the composition comprising fibrin monomer or noncrosslinked fibrin can be any source known or to be developed so long as the fibrin monomer can be converted to fibrin polymer or the noncrosslinked fibrin can be converted to crosslinked fibrin. Nonlimiting sources of compositions comprising fibrin monomer or noncrosslinked fibrin are blood, preferably mammalian blood and even more preferably human blood, cell cultures that secrete fibrinogen and recombinant fibrinogen, with blood being preferred. Blood can be any form of blood including, for example, whole blood or prepared fibrinogen preparations. Also, blood can be utilized to prepare an autologous fibrin sealant.

It has been observed that a composition comprising noncrosslinked fibrin I, either as fibrin I monomer or fibrin I polymer, prepared from whole blood as described below can be converted to crosslinked fibrin II without the addition of thrombin, factor XIII and other necessary substances for blood coagulation! It is believed that this is due to the fact that the composition comprising noncrosslinked fibrin I prepared from whole blood retains sufficient quantities of prothrombin, factor XIII and such other necessary substances from the plasma such that the noncrosslinked fibrin I can be converted to crosslinked fibrin II without the addition of exogeneous thrombin and factor XIII. This endogenous prothrombin and factor XIII can be utilized in the fibrin sealant of the subject invention as components of the composition comprising fibrin monomer or noncrosslinked fibrin.

However, it should be noted that sufficient quantities of this endogenous thrombin and factor XIII are not retained so as to convert fibrinogen to crosslinked fibrin II at a reaction rate that is suitable for a fibrin sealant. It is believed that more thrombin is required to convert fibrinogen to crosslinked fibrin II than to convert noncrosslinked fibrin I to crosslinked fibrin II at an equivalent reaction rate.

Each one of such three sources contains fibrinogen, which can be converted to the fibrin monomer or noncrosslinked fibrin. In addition to such conversion step, the resultant composition that contains the fibrin monomer or noncrosslinked fibrin must be in a concentrated form. It is preferred that the concentration of the fibrin monomer be no less than about 10 mg/ml, more preferably from about 20 mg/ml to about 200 mg/ml, even more preferably from about 20 mg/ml to about 100 mg/ml and most preferably from about 25 mg/ml to about 50 mg/ml.

In addition, it is preferred that the fibrin monomer or noncrosslinked fibrin be nondynamic. For the purpose of the present invention a nondynamic composition comprising noncrosslinked fibrin means that the noncrosslinked fibrin in such composition does not crosslink for at least about 1.5 minutes, preferably for at least about 3 minutes and more preferably for at least about 30 minutes after preparation of such composition. For the purpose of the present invention a nondynamic composition comprising fibrin monomer means that the fibrin monomer in such composition does not polymerize for at least about 1.5 minutes, preferably for at least about 3 minutes, more preferably for at least about 30 minutes and even more preferably at least about 2 hours after the preparation of the composition. In fact, it should be noted that the composition comprising fibrin monomer can be nondynamic for at least several days, i.e., about 72 hours, after its preparation!

PREPARATION AND CONCENTRATION OF A COMPOSITION COMPRISING FIBRIN MONOMER OR NONCROSSLINKED FIBRIN FROM BLOOD

The composition comprising fibrin monomer or noncrosslinked fibrin can be prepared from blood. The method can result in a hydrogen bonded fibrin polymer, which is a form of noncrosslinked fibrin. Such polymer can then be utilized as a component of the fibrin sealant or be converted to fibrin monomer by a process referred to as solubilization, all as described hereinbelow. Also, it is preferred that the composition comprising fibrin monomer or noncrosslinked fibrin be prepared in a sterile environment.

Compositions comprising fibrin monomer or noncrosslinked fibrin can be prepared from whole blood by withdrawing blood from a donor and preferably in the presence of an anticoagulant. Any anticoagulant can be utilized. Nonlimiting examples of anticoagulants are heparin, EDTA, hirudin, citrate or any other agent that can, directly or indirectly, prevent the formation of thrombin, with citrate being preferred.

The plasma, which contains the fibrinogen, is then separated from the whole blood. Any separation technique can be utilized, for example, sedimentation, centrifugation or filtration. Centrifugation can be carried out at about 3,000 g. for about 10 minutes. However, if it is desired to obtain plasma rich in platelets, centrifugation can be carried out at lower g force, e.g., 500 g for about 20 minutes. The supernatant, which contains the plasma, can be removed by standard techniques.

Filtration can be carried out by passing the whole blood through a suitable filter that separates blood cells from plasma. It is preferred that the filter be a microporous membrane exhibiting good protein transmission.

The resultant plasma is then treated to convert the fibrinogen to fibrin monomer or noncrosslinked fibrin. This conversion can be carried out by any technique that-is known or to be developed.

A preferred technique to produce fibrin monomer or noncrosslinked fibrin is by means of a thrombin-like enzyme, which includes thrombin. A thrombin-like enzyme is any enzyme that can catalyze the formation of fibrin from fibrinogen. A common source of thrombin-like enzymes are snake venoms. Preferably, the thrombin-like enzyme is purified from the snake venom. Depending on the choice of thrombin-like enzyme, such thrombin-like enzyme can release fibrinopeptide A—which forms fibrin I—fibrinopeptide B—which forms des BB fibrin—or both fibrinopeptide A and B—which forms fibrin II. It should be noted that those thrombin-like enzymes that release fibrinopeptide A and B may do so at different rates. Thus, the resultant composition could be, for example, a mixture of fibrin II and fibrin I or a mixture of fibrin II and des BB fibrin.

TABLE I is a nonlimiting list of the sources of the snake venoms that can be utilized in the subject invention, the name of the thrombin-like enzyme and which fibrinopeptide(s) is released by treatment with the enzyme.

TABLE 1

| SOURCE | NAME | FIBRINOPEPTIDE RELEASED |
| --- | --- | --- |
| Agkistrodon acutus | Acutin | A |
| A. contortrix contortrix | Venzyme | B, (A)* |
| A. halys Pallas | | B, (A)* |
| A. (Calloselasma) rhodostoma | Ancrod, Arvin | A |
| Bothrops asper (B. atrax) | Asperase | A |
| B. Atrox | Batroxobin, Reptilase -Reagent | A |
| B. insularis | | A, B |
| B. jararaca | Botropase | A |
| B. Moojeni (B. Atrox) | Batroxobin, Defibrase | A |
| Lachesis muta muta | | A, B |
| Crotalus adamanteus | Crotalase | A |
| C. durissus terrificus | | A |
| Trimeresurus flavoviridis | Flavoxobin | A |
| T. gramineus | | A |
| Bitis gabonica | Gabonase | A, B |

*( ) means low activity.

For a review of thrombin-like enzymes from snake venoms, see H. Pirkle and K. Stocker, Thrombosis and Haemostasis, 65(4):444–450 (1991).

The preferred thrombin-like enzymes are Batroxobin, especially from *B. Moojeni, B. Maranhao* and *B. atrox* and Ancrod, especially from *A. rhodostoma*.

The fibrin monomer or noncrosslinked fibrin can be prepared by contacting the plasma with the thrombin-like enzyme, thereby permitting the fibrinogen in the plasma to be converted to a fibrin monomer. However, the resultant fibrin monomer spontaneously polymerizes to form a hydrogen bonded polymer in the form of a gel, which separates from the remaining serum, which is a solution. The gel is a form of the composition comprising noncrosslinked fibrin.

This noncrosslinked fibrin gel can be harvested by, for example, centrifugation (3,000 g. for 10 minutes), direct manual separation of the noncrosslinked fibrin from the serum, filtration, directly or under pressure, followed by the removal of the separated serum. (A 1–100 micron pore size filter can be utilized, for example, a sintered polypropylene 20 micron pore size filter from Porex, Inc., a teflon 20–70 micron pore size filter from Fluorotechniques, Inc. or a nylon 66 22–46 micron pore size filter from Costar, Inc.).

This harvestation separates the noncrosslinked fibrin gel from serum, which is a solution, and, thereby, concentrates the noncrosslinked fibrin gel vis-a-vis the plasma. It should be noted that the noncrosslinked fibrin gel retains at least some prothrombin, factor XIII, and such other necessary substances from the plasma such that the noncrosslinked fibrin I can be converted to crosslinked fibrin II without the addition of exogenous thrombin or factor XIII. This endogenous prothrombin and factor XIII can be utilized in the fibrin sealant of the subject invention as components of the composition comprising fibrin monomer or noncrosslinked fibrin.

The force of centrifugation or pressure of filtration during harvestation will determine how much of the serum is removed from the noncrosslinked fibrin gel, with the higher such force or pressure, the more concentrated the resulting noncrosslinked fibrin gel. However, it is preferred that such force or pressure not be so great that the prothrombin and factor XIII are removed from the noncrosslinked fibrin gel.

The noncrosslinked fibrin gel is now ready for use as a component of the fibrin sealant as a form of the composition comprising noncrosslinked fibrin. It has been observed that when such composition is prepared from whole blood, from about 60% to about 90% of the original fibrinogen is present in the composition, but, of course, in the form of a noncrosslinked fibrin.

The composition comprising the noncrosslinked fibrin can be utilized immediately after it is prepared. In fact, it is particularly preferred to utilize such composition immediately after its preparation when the composition is autologous. If the composition is not utilized immediately after its preparation, the composition can be stored. Storage of the composition requires that the composition be preserved by, for example, freezing or lyophilizing the composition or holding the composition at 4° C. The composition in frozen or lyophilized form will be stable for a period of months. When the composition is held at 4° C., it is believed that the composition is stable for at least a period of days.

If the composition is frozen, the composition must be thawed prior to the time of use.

This technique that results in the formation of the noncrosslinked fibrin gel converts the fibrinogen to the noncrosslinked fibrin gel and concentrates such gel in essentially one step. Alternatively, and less preferred, one can concentrate fibrinogen by conventional techniques, e.g., cryoprecipitation and precipitation using various reagents, e.g., polyethylene glycol, ether, ethanol, ammonium sulfate or glycine. The concentrated fibrinogen can then be converted to the noncrosslinked fibrin gel by the techniques described above or, preferably, since the fibrinogen is already concentrated, then the fibrinogen can be converted to a composition comprising fibrin monomer without the need to first form the noncrosslinked fibrin gel. This can be carried out by contacting the concentrated fibrinogen with a chaotropic agent to obtain a fibrinogen solution.

The chaotropic agent is necessary to prevent the fibrin monomer, which is formed upon contact of the fibrinogen with the thrombin-like enzyme, from spontaneously polymerizing. The chaotropic agent is mixed with such fibrinogen composition and then agitated for about 1 to 2 minutes to form the fibrinogen solution. The fibrinogen can then be converted to a fibrin monomer by, for example, a thrombin-like enzyme, as described above, or by a thrombin-like enzyme immobilized on a support, as described below.

Suitable chaotropic agents include urea, sodium bromide, guanidine hydrochloride, KCNS, potassium iodide and potassium bromide. The preferred concentration of the chaotropic agent is from about 0.2 to about 6.0 molar and most preferably from about 0.3 to about 2.0 molar. It is preferred to utilize the least amount of chaotropic agent possible that still prevents the fibrin monomer from spontaneously polymerizing.

It should be noted that it is preferred that a source of calcium ions not be added to the chaotropic agent until it is desired to convert the fibrin monomer to fibrin polymer, as described below. This ensures that the fibrin monomer will not crosslink due to activation of any endogenous blood coagulation factors.

IMMOBILIZATION OF THROMBIN-LIKE ENZYME ON A SUPPORT

In a preferred embodiment, the thrombin-like enzyme is immobilized on a support. Such embodiment is preferred because one can readily separate the immobilized enzyme from the plasma, thereby preventing the composition comprising noncrosslinked fibrin from being contaminated by the enzyme.

Any support to which the thrombin-like enzyme can be attached can be utilized in the subject invention. Nonlimiting examples of suitable supports are cellulose, polydextrans, agarose, polystyrenes, silica, polyacrylic acids, polyacrylamides, polyvinylalcohols, glass beads, polytetrafluorethylene, polycarbonate, collagen, cellulose derivatives, teflon and their composites, with silica polystyrene and agarose being preferred and agarose being most preferred.

In another preferred embodiment the thrombin-like enzyme is attached to a support that is a filter or on one side of the filter and attached to another support, e.g., a bead. Otherwise, the thrombin-like enzyme will pass through the filter. Thus, the pore size of the filter should be such that the immobilized thrombin-like enzyme cannot pass through the filter, but the noncrosslinked fibrin can pass through the filter. The noncrosslinked fibrin is prepared by contacting the plasma with the thrombin-like enzyme on one side of the filter to form a fibrin monomer, which, along with the rest of the plasma, passes through the filter. Thus, the resulting composition comprising noncrosslinked fibrin is necessarily separated from the thrombin-like enzyme. The fibrin monomer, after passage through the filter, spontaneously polymerizes to form a noncrosslinked fibrin polymer.

In order to immobilize the thrombin-like enzyme to a support, the support must be activated. This can be carried out by any suitable technique. For example, various activation chemistries available for derivatizing supports are:

diazonium groups, isocyanate groups, acid chloride groups, acid anhydride groups, sulphonyl chloride groups, dinitro fluorophenyl groups, isothiocyanate groups, hydroxyl groups, amino groups, n-hydroxysuccinimide groups, triazine groups, hydrazino groups, carbodiimide groups, silane groups and cyanogen bromide. See (a) Pentapharm Patent DT 2440 254 A1; (b) P. D. G. Dean, W. S. Johnson and F. A. Middle (Editors) (1991) IRL Press Oxford—Affinity Chromatography—A practical approach—chapter 2—Activation Procedures, the disclosures of which are incorporated herein by reference.

The preferred activation chemistry is by means of a hydrazide group. The use of a hydrazide activated support results in a maximal percentage (at least about 30% to about 50% as measured by the S2238 assay—See Axelsson G. et al., Thromb. Haemost., 36:517(1976)) of the thrombin-like enzyme retaining its activity with essentially no enzyme leaching. Also, low pH values, e.g., pH 4–6, can be utilized for enzyme coupling to prevent enzyme degradation.

Generally, the support is activated by a highly reactive compound, which subsequently reacts with a functional group of a ligand, e.g., —OH, —NH$_2$, —SH, —COOH, —CHO to form a covalent linkage. The preferred activation chemistries for use in the subject invention are:

(a) by means of a triazine group and preferably triazine halogenide groups;

(b) by means of a tresyl chloride group;

(c) by means of a carbonyldiimidazole group;

(d) by means of a cyanogen bromide group; and (e) by means of a hydrazide or amino group.

In (a)–(d), the protein is coupled via reaction with —NH$_2$, —SH, or —OH groups, whereas in (e), the protein is coupled via an oxidized carbohydrate moiety, i.e., —CHO. The use of these chemistries results in a maximal percentage (at least about 30% to about 50% as measured by the S2238 assay) of the thrombin-like enzyme retaining its activity with essentially no enzyme leaching.

For triazine activation two different methods were used. The first method involved linking the triazine ring directly to surface OH groups. This is similar to the CNBr activation method employed, where surface diol groups were reacted with CNBr. For triazine activation, OH groups of agarose were reacted with triazine (cyanuric chloride).

Generally, the support is activated by a highly reactive compound, which subsequently reacts with a functional group of the ligand, e.g., —OH, —NH$_2$, —SH, —CHO, to form a covalent linkage. Remaining active groups, which have no thrombin-like enzyme attached, can be, but it is not essential, blocked with non-reactive compounds such as ethanolamine, acetic anhydride or glycine.

The preferred activation chemistries for use in the subject invention are:

(a) Cyanogen bromide activation followed by direct coupling of enzyme via —NH$_2$ groups on the protein.

(b) Activation of the support with monochlorotriazine followed by coupling of an enzyme via —NH$_2$, —OH or —SH groups.

(c) Activation of the support with dichlorotriazine followed by coupling of the enzyme via —NH$_2$, —OH or —SH groups.

(d) Tresyl chloride activation of the support followed by coupling of the enzyme via —NH$_2$, —OH or —SH.

(e) Activation of the support with adipic acid hydrazide or hydrazine followed by coupling of oxidised enzyme via —CHO groups.

(f) Activation of the support with an amino ligand followed by coupling of oxidised enzyme via —CHO groups.

All the above preferred methodologies employ agarose as the support, however, it is possible to use silica. When using this support, the preferred activation chemistries are:

(a) Gamma—glycidoxypropyltrimethoxysilane activation with direct coupling of the thrombin-like enzyme via —NH$_2$ groups on the protein.

(b) Cyanogen bromide activation followed by direct coupling of enzyme via —NH$_2$ groups on the protein.

(c) Gamma—glycidoxytrimethoxysilane activation followed by opening of the epoxide ring to form a diol group, which can be subsequently activated with cyanogen bromide. Direct coupling of the enzyme can be achieved via —NH$_2$ groups on the protein.

(d) Gamma—glycidoxypropyltrimethoxysilane activation followed by preparation of amino-silica by treatment with ammonia solution.

The amino-silica can be subsequently activated with cyanuric chloride (triazine) and the enzyme coupled via —NH$_2$, —OH or —SH groups.

COUPLING OF ENZYME TO ACTIVATED SUPPORT

Coupling of the enzyme to the activated support must be buffered at a certain pH to obtain optimal enzyme binding. Generally, with standard activation techniques such as gamma-glycidoxy-propyltri-methoxysilane coupling of enzyme to activated support and cyanogen bromide coupling of any protein to active groups requires buffering at a pH 1–2 units higher than the pKa of the primary and secondary amines of the enzyme. However, the use of cyanuric chloride as the activator enables the use of much lower pH buffers (optimal coupling pH is 4–6). Another method of coupling glycoproteins such as batroxobin to an inert support is via their carbohydrate moieties. This involves first the oxidation of the sugar group to —CHO groups followed by direct coupling at acid pH to an amino group such as hydrazide. A wide range of coupling buffers can be used. See, for example, Table 2.

TABLE 2

EXAMPLES OF COUPLING BUFFERS USED IN ENZYME IMMOBILIZATION TO SILICA AND AGAROSE SUPPORTS

| SUPPORT | ACTIVATION METHOD | COUPLING BUFFER |
|---|---|---|
| Silica | Gamma-glycidoxypropyl-trimethoxysilane | 0.1M Sodium bicarbonate pH 8–9<br>10 mM HEPES pH 7.0 |
| Silica | γ-glycidoxypropyl-trimethoxysilane + cyanogen bromide | 0.1M Sodium bicarbonate pH 8–9<br>10 mM HEPES pH 7.0 |
| Silica | Cyanogen Bromide | Water pH 7.0<br>0.1M Sodium bicarbonate pH 7–9<br>10 mM HEPES pH 7.0 |
| Agarose | Monochlorotriazine | 50 mM Sodium Acetate/1M NaCl pH 4.0 |
| Agarose | Dichlorotriazine | 0.1M Potassium phosphate/1M NaCl pH 8.0–9.0 |
| Agarose | Tresyl chloride | 50 mM Potassium phosphate/0.5M NaCl pH 7.7 |
| Agarose | Hydrazide | 50 mM Sodium Acetate pH 5.5<br>10 mM NaBH$_4$ |
| Agarose | Amine | 50 mM Sodium Acetate pH 5.5<br>10 mM NaBH$_4$ |

BLOCKING AND DEACTIVATING REMAINING ACTIVE GROUPS

After activation the support will possess more active sites than required for enzyme coupling. These sites, if not deactivated, may covalently bind contaminating proteins, which might affect the biological function of the immobilized enzyme.

Excess groups can be deactivated by the covalent coupling of small, noninterfering amines such as ethanolamine.

If hydrazide or amino activated supports are employed, blocking of residual reactive groups following enzyme coupling can be achieved by use of acetic anhydride.

Depending on the method of immobilization and the support, enzyme inactivation occurs during the immobilization process. Employing a silica support with the most desirable activation chemistry (e.g., cyanogen bromide), up to 80–90% of enzyme activity is lost. However, the use of agarose as the support with cyanuric chloride activation results in less loss of of enzyme activity.

CHARACTERIZATION

In order to characterize the efficacy of the immobilized enzyme on the support, two methods can be utilized to assess the amount of active enzyme immobilized on the support; the Clot Time Assay—Clauss A., *Acta Haematol.*, 17:237 (1957) and the S2238 Assay—See Axelsson G. et al., *Thromb. Haemost.*, 36:517 (1976).

To assess the leaching of the enzyme from the support, the following assay can be utilized.

Leaching can be assayed by radiolabelling the thrombin-like enzyme, e.g., $I^{125}$ batroxobin. However, prior to carrying out the leaching assay, it is necessary to remove any unbound radiolabel. This can be achieved by sequentially washing the support with: 50 ml 50 mM sodium acetate pH 5.5, 100 ml 50 mM glycine/1M sodium chloride pH 3.0, 100 ml 50 mM sodium carbonate/1M sodium chloride pH 10.0, 100 ml 50 mM sodium phosphate/1M sodium chloride pH 7.0, 100 ml water and 100 ml 50 mM sodium phosphate/1M sodium chloride pH 7.0. After such a washing procedure, there was no detectable radiolabel in the washings, with $\geq$50% of the initial radiolabelled enzyme coupled to the support.

FORMATION OF NONCROSSLINKED FIBRIN (a) Amount of Enzyme Required

The amount of enzyme required for the treatment of 30–70 ml plasma (obtained from 60–150 ml whole blood) is 30–200 units after about 10–15 minutes mixing.

If agarose is employed as the support matrix, 30–200 U of batroxobin results in the formation of noncrosslinked fibrin in about 7–20 minutes. This system employs hydrazide activation and 0.25 g–1.0 g of dry agarose. In this case no blocking of remaining active groups is required.

(b) Reaction of Immobilized Enzyme with Plasma Fibrinogen

Generally, the reaction of the immobilized enzyme with fibrinogen in plasma is performed as follows: approximately 30–70 ml of plasma is added to a known quantity of a dried support, which contains the immobilized thrombin-like enzyme. The suspension is mixed gently (rotation on a spiral mixer or hand mixing) for approximately 7–20 minutes. During this time fibrinogen in the plasma is cleaved by the immobilized enzyme to release fibrinopeptide A and/or fibrinopeptide B resulting in the formation of a hydrogen bonded fibrin I polymer, hydrogen bonded des BB fibrin polymer or hydrogen bonded fibrin II polymer wherein each polymer is associated with the immobilized enzyme.

As described above, the hydrogen bonded fibrin polymer is in the form of a gel and can be harvested by, for example, centrifugation (3,000 g. for 10 minutes) or filtration (through a 1–50 micron membrane filter). Such harvestation separates the hydrogen bonded fibrin polymer from serum and, thereby, concentrates the polymer.

THE PREVENTION OF FORMATION OF CROSSLINKED FIBRIN

It should be noted that if a thrombin-like enzyme is utilized in plasma that results in the activation of factor XIII, then it is preferred that the plasma composition be modified at the time the thrombin-like enzyme is utilized so as to prevent the noncrosslinked fibrin, e.g., noncrosslinked fibrin I or II, from forming crosslinked fibrin, e.g., crosslinked fibrin I or II. Of course, it may not be necessary to modify the plasma composition if such composition is utilized as a fibrin sealant immediately after the fibrinogen has been converted to noncrosslinked fibrin.

The plasma composition can be modified to prevent the crosslinking of the noncrosslinked fibrin by any technique that is known or to be developed. This can be carried out-by blocking the endogenous thrombin that can activate the factor XIII, e.g., hirudin or thrombin inhibitors, or blocking the action of activated factor XIII, e.g., by means of heavy metals (Hg), thiomerosal or inhibitory antibodies. Crosslinking of fibrin I or II requires the presence of calcium ions. Thus, if the calcium is removed from the plasma composition, crosslinking of the fibrin I or II can be inhibited. See Carr et al., *J. Biochem.*, 239:513 (1986); Kaminski et al., *J, Biol. Chem.* 258:10530 (1983) and Kanaide et al. 13:229 (1982). Calcium chelators can be added to the composition to prevent the crosslinking of the fibrin I or II. Such chelators bind to the calcium, thereby preventing the crosslinking. Any calcium chelator can be utilized. Nonlimiting examples of calcium chelators include citric acid, saccharic acid, ethylenediaminetetraacetic acid (EDTA), nitrilotriacetic acid (NTA), hydroxyethylenediaminetriacetic acid (HEEDTA), ethylenediaminedi[o-hydroxyphenylacetic acid] (EDDHA), ethylene-glycolbis (2-aminoethylether) tetraacetic acid (EGTA), diethylenetriaminepentaacetic acid (DTPA), 1,2-diaminocyclohexanetetraacetic acid (DCTA), N,N-bishydroxyethylglycine, 4-(2-hydroxyethyl)-1-piperazineethanesulfonic acid (HEPES) and N-hydroxyethyliminodiacetic acid (HIMDA) and salts thereof, with salts of citric acid being preferred.

PREPARATION AND CONCENTRATION OF FIBRIN MONOMER OR NONCROSSLINKED FIBRIN FROM CELL CULTURES THAT SECRETE FIBRINOGEN

Any cell culture that can secrete fibrinogen can be utilized in the subject invention. The fibrinogen in the cell culture can be converted to fibrin monomer or noncrosslinked fibrin by the same techniques as those described above with respect to plasma. However, prior to such conversion, it is preferred that the cellular debris be removed.

The process can be carried out as follows: HEPG2 cells are grown and maintained as described by standard texts on mammalian cell culture. Also, see Liu et al., *Cytotechnology*, 5:129–139 (1991). The cells are seeded into flasks at a split ratio between 1:4 to 1:8 in Minimal Essential Medium containing 10% calf serum and buffered with 5% $CO_2$.

After 24–36h growth at 37° C., the medium is removed and replaced with serum free medium containing a suitable protease inhibitor and 2 IU/ml heparin. Culture is continued for further 24h periods with three consecutive changes of serum free media.

The conditioned media is centrifuged at 3,000 g for 10 minutes to remove any cell debris and the clarified supernatant, which contains fibrinogen, is then gently mixed with a thrombin-like enzyme for 4–5 hours. Preferably, the thrombin-like enzyme is immobilized. A ratio of from about 1.0 ml to about 50 ml., settled volume agarose-thrombin-like enzyme per 500 ml media is suitable. As described above, supports other than agarose can be utilized. The resulting fibrin monomer spontaneously polymerizes and is enmeshed around the immobile support.

The supernatant, which now contains no fibrinogen, is decanted from the support/fibrin gel, which is then washed successfully with four changes of NaCl-0.15 M. at a ratio of from about 10 ml. to about 100 ml. per 1.0 ml original settled volume of support. The washed gel is then semi-dehydrated using a sintered glass funnel under vacuum.

The use of cell cultures that can secrete fibrinogen are particularly preferred when a composition comprising a fibrin monomer is utilized. This is because it is believed that such composition can be utilized to form a fibrin polymer that is useful as a fibrin sealant, regardless of whether the fibrin polymer ultimately crosslinks. Thus, since such cell culture does not contain factor XIII, which is essential for crosslinking, no exogenous factor XIII need be added to make an effective fibrin sealant.

PREPARATION AND CONCENTRATION OF FIBRIN MONOMER OR NONCROSSLINKED FIBRIN FROM RECOMBINANT FIBRINOGEN

The noncrosslinked fibrin composition can also be prepared from recombinant fibrinogen. Only recently fibrinogen has been made by recombinant DNA techniques. See S. Roy et al., *The Journal of Biological Chemistry*, 266:4758–4763 (1991), the contents of which are incorporated herein by reference. Roy et al. appears to be the first group to express all three chains of fibrinogen and teach that COS cells express, assemble and secrete the chains in a form that is capable of forming a thrombin-induced clot. The resultant fibrinogen composition can then be utilized to produce the composition comprising fibrin monomer or noncrosslinked fibrin by the same techniques as described hereinabove with respect to cell cultures that secrete fibrinogen. However, it is preferred that prior to the formation of the composition comprising fibrin monomer or non-crosslinked fibrin, the cellular debris be removed by the same techniques as described above with respect to cell cultures. The cellular debris can be removed by centrifugation or filtration.

The use of recombinant fibrinogen is particularly preferred when a composition comprising a fibrin monomer is utilized. This is because it is believed that such composition can be utilized to form a fibrin polymer that is useful as a fibrin sealant, regardless of whether the fibrin polymer ultimately crosslinks. Since the recombinant fibrinogen cell culture does not contain factor XIII, which is essential for crosslinking, no exogenous factor XIII need be added to make an effective fibrin sealant.

SOLUBILIZATION OF NONCROSSLINKED FIBRIN

The conversion of fibrinogen to noncrosslinked fibrin by, for example, a thrombin-like enzyme, results in the formation of the fibrin in the form of a fibrin hydrogen-bonded polymer. However, as discussed above, it is preferred that the composition comprising noncrosslinked fibrin, and it is essential for the composition comprising fibrin monomer, be in oligomeric or monomeric form. This can be carried out by solubilization of the composition comprising noncrosslinked fibrin.

Solubilization is particularly preferred when the non-crosslinked fibrin is formed by means of a thrombin-like enzyme that is immobilized on a support. This is due to the fact that the use of a thrombin-like enzyme immobilized on a support generally results in the noncrosslinked fibrin hydrogen-bonded polymer being associated with such immobilized enzyme. Thus, since it is preferred that the support not be contained in the resulting composition, solubilization permits one to also remove from the composition comprising noncrosslinked fibrin the support, along with the immobilized enzyme.

Solubilization can be carried out by any technique that is known or to be developed that results in a fibrin monomer. Solubilization can be carried out by contacting the composition comprising noncrosslinked fibrin with a suitable acid buffer solution, preferably an acid buffer having a pH of less than about 5 and preferably from about 1 to about 5. Nonlimiting examples of suitable acid buffer solutions include acetic acid, succinic acid, glucuronic acid, cysteic acid, crotonic acid, itaconic acid, glutamic acid, formic acid, aspartic acid, adipic acid and salts thereof and with succinic acid, aspartic acid, adipic acid and salts of acetic acid being preferred and most preferably sodium acetate. It has been observed that the preferred acid buffers functioned much more efficiently than that of other acid buffers that were tested.

The preferred concentration of the acid buffer is from about 0.02M to about 1M and most preferably from about 0.1M to about 0.3M. Such preferred concentration renders the ionic strength of the composition more biologically compatible.

It is preferred to utilize the least volume of acid buffer possible that still solubilizes the noncrosslinked fibrin to form an aqueous solution comprising fibrin monomer. This results in an aqueous solution comprising fibrin monomer that is highly concentrated in fibrin monomer. Generally, from about 1 ml to about 4 ml of acid buffer per about 1 ml of composition comprising noncrosslinked fibrin is required.

The acid buffer is mixed with the noncrosslinked fibrin and then agitated vigorously for about 1 to 2 minutes to ensure that solubilization is complete.

Solubilization can also be carried out at neutral pH by means of a chaotropic agent. Suitable chaotropic agents include urea, sodium bromide, guanidine hydrochloride, KCNS, potassium iodide and potassium bromide. The preferred concentration of the chaotropic agent is from about 0.2 to about 6.0 molar and most preferably from about 3.5 to about 5.0 molar.

AS with the acid buffer, it is preferred to utilize the least amount of chaotropic agent possible that still solubilizes the noncrosslinked fibrin. Generally, from about 1.0 ml to about 1.5 ml of chaotropic agent per about 1 ml of composition comprising noncrosslinked fibrin is required.

The chaotropic agent is mixed with such composition and then agitated vigorously for about 1 to 2 minutes to ensure that solubilization is complete.

Accordingly, solubilization results in a composition comprising a fibrin monomer and, in particular, an aqueous solution comprising fibrin monomer. It is preferred that the fibrin monomer concentration in the aqueous solution be no less than about 10 mg/ml, more preferably from about 20 mg/ml to about 200 mg/ml, even more preferably from about 20 mg/ml to about 100 mg/ml and most preferably from about 25 mg/ml to about 50 mg/ml.

If a thrombin-like enzyme immobilized on a support is utilized that results in such enzyme being present in the composition comprising noncrosslinked fibrin, after solubilization the immobilized enzyme can be removed from the composition comprising the fibrin monomer. This can be carried out by, for example, filtration through any suitable filter that can separate the enzyme. Suitable filters include a sintered polypropylene 20 micron pore size filter from Porex, Inc., a teflon 20–70 micron pore size filter from Fluorotechniques, Inc. or a nylon 66 22–46 micron pore size filter from Costar, Inc.

An alternative method for ensuring that no thrombin-like enzyme, e.g., batroxobin, is present in the composition comprising fibrin monomer is to use a soluble thrombin-like enzyme in the system and remove the enzyme following solubilization of the fibrin hydrogen-bonded polymer. The removal of the enzyme can be achieved by use of an affinity matrix, e.g., a ligand bound to an inert support that has a specific affinity for the thrombin-like enzyme or an ion exchange or hydrophobic interaction support or most effectively using the avidin-biotin system. The biotin-avidin interaction exhibits one of the strongest non-covalent binding constants ($K_{DIS}=10^{-15}$M) seen in nature. See E. A. Bayer and M. Wilchek, *Methods of Biochemical Anaylsis*, 26:1 (1980).

In this process, biotin is covalently bound to, for example, batroxobin and the biotin-batroxobin conjugate (which is soluble) is directly reacted with plasma, e.g., 10 BU plus 50 ml plasma reacted at 37° C. for 10 minutes. The Fibrin I polymer produced is harvested by centrifugation or filtration and resolubilized in approximately 4 ml 0.2M sodium acetate pH 4.0 containing 30 mM calcium chloride. To the Fibrin I solution is added a molar excess of avidin coupled to an inert support such as agarose. The agarose:avidin:biotin-batroxobin complex is then separated from the Fibrin I by centrifugation or filtration resulting in a composition comprising fibrin monomer that is substantially free of batroxobin, which can be repolymerised as described below to generate a fibrin sealant.

Accordingly, in one embodiment of the present invention, the composition comprising fibrin monomer is substantially free of the thrombin-like enzyme. By substantially free is meant either that all of the thrombin-like enzyme has been removed, or that any thrombin-like enzyme remaining in the composition is at levels insufficient to provide any undesired pharmacological effect. Thus, compositions of this invention desired to be "substantially free" may contain thrombin-like enzyme in an amount between about zero and 10 percent of the original enzyme and preferably between about zero and 2 percent of the thrombin-like enzyme used to prepare the fibrin monomer composition.

Although these embodiments describe compositions wherein the thrombin-like enzyme has been removed following the desired conversion to soluble fibrin, compositions retaining most or all of the thrombin-like enzyme are also believed useful and, as such, are a part of the present invention.

The composition comprising fibrin monomer is now ready for use as a component of the fibrin sealant. It has been observed that when such composition is prepared from whole blood, from about 60% to about 90% of the original fibrinogen is present in the composition, but, of course, in the form of fibrin monomer.

The composition comprising the fibrin monomer can be utilized immediately after it is prepared. In fact, it is particularly preferred to utilize such composition immediately after its preparation when the composition is autologous. If the composition is not utilized immediately after its preparation, the composition can be stored. Storage of the composition requires that the composition be preserved by, for example, freezing or lyophilizing the composition or holding the composition at 4° C. It is believed that the composition in frozen or lyophilized form will be stable for a period of months. When the composition is held at 4° C., it is believed that the composition is stable for at least a period of days.

If the composition is frozen, the composition must be thawed at the time of use. If the composition is lyophilized, at time of use, it is preferred that the composition be reconstituted by the addition of the same acid buffer that was utilized in the solubilization step if that acid was volatile, e.g., acetic acid, or if a choatropic agent was utilized, by the addition of distilled water. As in the solubilization step, in reconstitution the least amount of acid buffer solution or distilled water should be utilized that still results in the fibrin monomer being soluble. In fact, reconstituting a lyophilized composition comprising fibrin monomer can result in an aqueous solution comprising fibrin monomer wherein such monomer concentration is up to 200 mg/ml. Prior to lyophilization, a bulking agent, e.g., mannitol or lactose, can be added to the composition. Alternatively, the lyophilized composition can be utilized in lyophilized form. Such form is particularly preferred when it is desired to add adjuvants, e.g., antibiotics, to the composition.

The composition comprising fibrin monomer can be in virtually any form, for example, a solution, suspension, emulsion or solid, with a solution being preferred. Thus, for example, such composition can be a liquid, gel, paste or salve. Also, of course, the composition can be in the form of a "granule," for example, lyophilized fibrin monomer, that can be, but need not be, treated to form a solution, emulsion or suspension immediately prior to use.

Any suitable solvent can be utilized to form the solution, but, of course, it is preferred that the solvent be nontoxic. Nonlimiting examples of solvents include water, ethyl alcohol, glycerol and propylene glycol, with water being preferred.

An example of a suspension is that the composition comprising fibrin monomer can be mixed with organic solvents, e.g., ethanol, to a final ethanol concentration in excess of 3.0M and shaken. The fibrin monomer will precipitate and can be recovered by centrifugation. The precipitate should be washed with organic phase to remove the aqueous solution used in the solubilization step. An ethanolic suspension of monomeric fibrin can then be applied directly to a bandage or other carrier or even applied directly to a wound site. The organic phase is allowed to evaporate. In the case of a bandage or other carrier the suspension can be rehydrated by contacting with the site of application or some other means, and the fibrin allowed to polymerize.

Alternatively, an organic suspension of fibrin monomer prepared in a highly volatile phase, e.g., diethyl ether, might be atomized and delivered as a spray suspension to the desired site. It is preferable that the volatile phase is nonflammable. It is possible that an organic suspension of fibrin monomer could be delivered to the ear, nose, throat, or lungs by spray or breathing or delivered to a bleeding oesophageal or gastric lesion by injestion.

THE USES OF THE FIBRIN SEALANT OF THE SUBJECT INVENTION

The fibrin sealant of the subject invention is utilized by contacting the desired site with the composition comprising fibrin monomer or noncrosslinked fibrin and converting the fibrin monomer to fibrin polymer or noncrosslinked fibrin to crosslinked fibrin concurrently with said contacting step, thereby forming the fibrin clot.

For the purpose of the subject invention "desired site" is that location where one desires to form the fibrin clot. What or where the desired site is depends on the use of the fibrin sealant of the subject invention. Also, it should be noted that it is believed that the fibrin sealant can be utilized not only in humans but also in other mammals. Also, if the source of the fibrin sealant is blood, then it is preferred, but not essential, that the blood be derived from the same species that the fibrin sealant will be utilized.

The fibrin sealant of the subject invention can be utilized for any use that is known or to be developed for a fibrin sealant. The methods, kits or fibrin sealant of the subject invention can be used for connecting tissues or organs, stopping bleeding, healing wounds, sealing a surgical wound, use in vascular surgery include providing hemostasis for stitch hole bleeding of distal coronary artery anastomoses; left ventricular suture lines; aortotomy and cannulation sites; diffuse epimyocardial bleeding seen in reoperations; and oozing from venous bleeding sites, e.g. at atrial, caval, or right ventricular levels. The subject invention is also useful for sealing of dacron artery grafts prior to grafting, sealing tissues outside the body, producing fibrin rafts for cell growth, stopping bleeding from damaged spleens (thereby saving the organ), livers, and other parenchymatous organs; sealing tracheal and bronchial anastomoses and air leaks or lacerations of the lung, sealing bronchial stumps, bronchial fistulas and esophageal fistulas; for sutureless seamless healing ("Zipper" technique), and embolization in vascular radiology of intracerebral AVM's, liver AVM's, angiodysplasia of colon, esophageal varices, "pumping" GI bleeders secondary to peptic ulcers, etc. The subject invention is further useful for providing hemostasis in corneal transplants, nosebleeds, post tonsillectomies, teeth extractions and other applications. See G. F. Gestring and R. Lermer, *Vascular Surgery*, 294–304, September/October 1983. Also, the fibrin sealant of the subject invention is especially suited for individuals with coagulation defects.

The dosage of the composition comprising fibrin monomer or composition comprising noncrosslinked fibrin depends on the particular use of the fibrin sealant, but the dosage should be an effective amount for the composition to perform its intended use. Generally, for a composition comprising fibrin monomer that is an aqueous solution, it is believed that from about 3 ml to about 5 ml of such composition is sufficient to be an effective fibrin sealant. However, depending on the use of the composition, the dosage can range from about 0.05 ml to about 40 ml Also, if a composition comprising noncrosslinked fibrin in polymer form is utilized or the composition is in solid form, then the composition should contain that amount of fibrin that is in such aqueous solution.

THE ADMINISTRATION OF THE FIBRIN SEALANT OF THE SUBJECT INVENTION

For the purpose of the subject invention the conversion of the fibrin monomer to fibrin polymer or noncrosslinked fibrin to crosslinked fibrin "concurrently" with said contacting step means that such conversion step and such contacting step occur within a time period of each step so as to form the fibrin clot at the desired site. Thus, concurrently can mean that after the contacting step, the fibrin monomer is converted to fibrin polymer or the noncrosslinked fibrin is converted to crosslinked fibrin. This is carried out by contacting the composition comprising fibrin monomer or noncrosslinked fibrin, after such composition has been applied to the desired site, with a composition that can convert the fibrin monomer to fibrin polymer or the noncrosslinked fibrin to crosslinked fibrin. The conversion step should generally occur within about 0.5 minutes after the contacting step. Otherwise, the composition comprising the fibrin monomer or noncrosslinked fibrin, especially if the noncrosslinked fibrin is a fibrin monomer, may flow away from the desired site.

Concurrently can also mean that the contacting step and converting step take place simultaneously. This is carried out by contacting the desired site with the composition comprising the fibrin monomer or noncrosslinked fibrin at the same time that such composition is contacted with a composition that can convert the fibrin monomer to fibrin polymer or the noncrosslinked fibrin to crosslinked fibrin.

Finally, and preferably, concurrently can also mean that the conversion step can commence prior to the contacting step, albeit not so far prior to the contacting step that all of the fibrin monomer has been converted to fibrin polymer or all of the noncrosslinked fibrin has been converted to crosslinked fibrin. Otherwise, all of the fibrin monomer will be converted to fibrin polymer or all of the noncrosslinked fibrin will be converted to crosslinked fibrin, prior to the contacting step, which results in a very poor fibrin sealant. This embodiment is carried out by mixing the composition comprising the fibrin monomer or noncrosslinked fibrin with a composition that can convert the fibrin monomer to fibrin polymer or the noncrosslinked fibrin to crosslinked fibrin, prior to the contacting step. Since it takes about 30 seconds for the conversion step to be complete, the conversion step should not begin more than about 30 seconds and preferably not more than about 3 seconds prior to the contacting step. This embodiment is preferred because it ensures that the maximum amount of the composition comprising the fibrin monomer or noncrosslinked fibrin will remain at the desired site and yet also forms an excellent fibrin clot.

CONVERSION OF THE COMPOSITION COMPRISING FIBRIN MONOMER TO FIBRIN POLYMER OR NONCROSSLINKED FIBRIN TO CROSSLINKED FIBRIN

The conversion of the fibrin monomer to fibrin polymer or the noncrosslinked fibrin to crosslinked fibrin can be carried out by any technique that is known or to be developed. However, how the conversion step is carried out depends on the source of the composition comprising fibrin monomer or noncrosslinked fibrin e.g., whole blood or recombinant fibrinogen, the form of the fibrin monomer or noncrosslinked fibrin, e.g., fibrin I or des BB fibrin, and, to a lesser extent, whether the desired site will contain the patients blood or other body fluids at the time of use of the fibrin sealant.

Also, if a separate composition, such as an alkaline buffer, is utilized (discussed below) for the conversion step, then the method of the subject invention can be carried out with, for example, a double-barrelled syringe. The double-barrelled syringe can be Y-shaped, thereby permitting the mixing of the composition comprising fibrin monomer or noncrosslinked fibrin and the composition to be utilized in the conversion step to mix immediately prior to the contacting step. Also, rather than a Y-shaped double-barrelled syringe a double-barrelled syringe with two openings can be utilized. This permits the simultaneous contacting of the desired site and conversion to fibrin polymer or crosslinked fibrin to take place. Also, the compositions of the double-barrelled syringe can be sprayed onto the desired site. See H. B. Kram et al., *The American Surgeon*, 57:381 (1991).

BLOOD AS THE SOURCE OF THE COMPOSITION COMPRISING FIBRIN MONOMER OR NONCROSSLINKED FIBRIN

If the source of the composition comprising fibrin monomer or noncrosslinked fibrin is blood, then as discussed above, it is believed that the composition will retain enough prothrombin, factor XIII and other necessary substances to convert such fibrin monomer or noncrosslinked fibrin to crosslinked fibrin, e.g., activators of prothrombin. If the noncrosslinked fibrin is a fibrin polymer, i.e., the noncrosslinked fibrin has not been solubilized, the noncrosslinked fibrin can be converted to crosslinked fibrin by the activation of prothrombin and factor XIII of such composition to form crosslinked fibrin. Such activation can be carried out by contacting the composition with a source of calcium ions. Nonlimiting sources of calcium ions include calcium chloride, preferably at a concentration of 30 mM. Alternatively, and less preferred, the calcium ions can be supplied by the blood at the desired site.

If the noncrosslinked fibrin has been solubilized, i.e., is a fibrin monomer, how the fibrin monomer is converted to crosslinked fibrin depends on how the solubilization was carried out. If the noncrosslinked fibrin was solubilized by an acid buffer, the crosslinked fibrin can be formed by raising the pH of the composition comprising fibrin monomer such that the fibrin monomer can polymerize. This can be carried out by contacting such composition with any suitable alkaline buffer. Nonlimiting examples of suitable alkaline buffers include HEPES, sodium hydroxide, potassium hydroxide, calcium hydroxide, bicarbonate buffers such as sodium bicarbonate and potassium bicarbonate, tri-metal salts of citric acid, salts of acetic acid and salts of sulfuric acid. Preferred alkaline buffers include: 0.5–0.75M Sodium carbonate/bicarbonate pH 10–10.5, 0.5–0.75M Sodium bicarbonate/NaOH pH 10.0, 1.5M Glycine/NaOH pH 10.0, 0.5–1.0M Bis hydroxeythylaminoethane sulphonic acid (BES) pH 7.5, 1M Hydroxyethylpiperazine propane sulphonic acid (EPPS) pH 8.5, 0.5M Tricine pH 8.5, 1M Morpholino propane sulphonic acid (MOPS) pH 8.0, 1M Trishydroxymethyl aminoethane sulphonic acid (TES) pH 8.0 and 0.5M Cyclohexylaminoethane sulphonic acid (CHES) pH 10.0; with 0.5–0.75M Sodium carbonate/bicarbonate pH 10–10.5, 0.5–1.0M Bis hydroxeythylaminoethane sulphonic acid (BES) pH 7.5, 1M Hydroxyethylpiperazine propane sulphonic acid (EPPS) pH 8.5 and 1M Trishydroxymethyl aminoethane sulphonic acid (TES) pH 8.0 being most preferred.

The amount of alkaline buffer that is utilized should be enough to polymerize the noncrosslinked fibrin. It is preferred that about 10 parts to about one part of composition comprising fibrin monomer be mixed with about 1 part alkaline buffer. It is even more preferred that such ratio be about 9:1. It should be noted that the preferred ratio depends on the choice of buffer and the desired "strength" of the fibrin polymer. Of course, the desired strength of the fibrin polymer depends on the end-use of the fibrin sealant.

If the solubilization was carried out with a chaotropic agent, then the fibrin monomer can be converted to crosslinked fibrin by diluting the composition comprising fibrin monomer with, for example, distilled water. The dilution should be carried out such that the minimal amount of diluent is utilized. Generally; the resulting concentration of the chaotropic agent after dilution should be from about 0.5 to about 0.1 molar.

In addition to raising the pH or diluting the chaotropic agent of the composition comprising fibrin monomer, it is preferred that the prothrombin and factor XIII of such composition be activated to form the crosslinked fibrin. Such activation can be carried out by the contacting the composition with a source of calcium ions. The source of the calcium ions can be part of the alkaline buffer or part of the acid buffer that is utilized in the solubilization step. Nonlimiting sources of calcium ions include calcium chloride, preferably at a concentration of 30 mM. Alternatively, and less preferred, the source of calcium ions can be supplied by the blood at the desired site.

It should be noted that if the alkaline buffer is a carbonate/bicarbonate buffer, then the source of calcium ions must be added to the acid buffer during the solubilization step. This is due to the fact that the calcium chloride is not soluble in the carbonate/bicarbonate buffer. It is preferred that the concentration of calcium ions in the acid buffer solution be from about 5 millimolar to about 150 millimolar and more preferably from about 5 mM to about 50 mM.

It is believed that the resulting fibrin clot will be crosslinked fibrin II, regardless of which form of noncrosslinked fibrin, i.e., fibrin monomer or fibrin polymer, is present. However, if the form of noncrosslinked fibrin is des BB fibrin, then it is believed that in addition a source of additional thrombin may be required to convert des BB fibrin to crosslinked fibrin. Such a source of thrombin can be, for example, plasma from the patient wherein such plasma is added to the composition comprising noncrosslinked fibrin.

If the desired site contains blood and a composition comprising a fibrin monomer is utilized, i.e., the noncrosslinked fibrin has been solubilized, then this blood can be utilized as a diluent of the chaotropic agent or to raise the pH of the composition comprising fibrin monomer. Thus, no diluent or alkaline buffer need be utilized. In this embodiment, it is preferred that the source of calcium ions be contained in the acid buffer or chaotropic agent utilized in the solubilization step. Also, in this embodiment the composition comprising fibrin monomer can be placed on a solid support, e.g., bandage, suture, prosthesis, or dressing, that will be in contact with the desired site. Such support is then placed in contact with the desired site until, for example, the fibrin clot forms.

However, it should be noted, that if the composition comprising fibrin monomer does not retain enough prothrombin and factor XIII so as to form crosslinked fibrin, such composition is still useful as a fibrin sealant because the polymerization of fibrin monomer per se is useful to form a fibrin clot. Also, such composition can still be utilized to form crosslinked fibrin by the addition of a source of calcium ions and activated factor XIII (or precursors to activated factor XIII) and, optionally, thrombin. Such source of calcium ions, activated factor XIII and thrombin can be added to the compositions comprising fibrin monomer. The activated factor XIII can be added to the composition comprising fibrin monomer at a final concentration of from about 1.0 to about 20 units factor XIII per ml of composition comprising noncrosslinked fibrin. Alternatively, the factor XIII can be supplied by the blood or body fluids at the desired site or by the addition of autologous plasma to the composition comprising fibrin monomer. Nonlimiting sources of calcium ions include calcium chloride, preferably at a concentration of 30 mM. Alternatively, and less preferred, calcium ions can be supplied by the blood or body fluids at the desired site. From about 4 units to about 500 units of thrombin per ml. of composition comprising fibrin monomer can be added or the thrombin can be provided by the desired site.

CELL CULTURES THAT SECRETE FIBRINOGEN OR RECOMBINANT FIBRINOGEN AS THE SOURCE OF THE COMPOSITION COMPRISING FIBRIN MONOMER OR NONCROSSLINKED FIBRIN

If the source of the composition comprising noncrosslinked fibrin are cell cultures that secrete fibrinogen or recombinant fibrinogen, and the noncrosslinked fibrin is a fibrin polymer, i.e., the noncrosslinked fibrin has not been solubilized, then a source of calcium ions and activated factor XIII (or precursors to activated factor XIII) must be utilized to form crosslinked fibrin. Factor XIII must be utilized because these sources of noncrosslinked fibrin do not contain any factor XIII. The activated factor XIII can be added to the composition comprising noncrosslinked fibrin at a final concentration of from about 1.0 to about 20 units factor XIII per ml of composition comprising noncrosslinked fibrin. Alternatively, the factor XIII can be supplied by the blood or body fluids at the desired site or by the addition of autologous plasma to the composition comprising noncrosslinked fibrin. Nonlimiting sources of calcium ions include calcium chloride, preferably at a concentration of 30 mM. Alternatively, and less preferred, calcium ions can be supplied by the blood or body fluids at the desired site. Also, as an option, thrombin can be added to such composition in order to ensure that crosslinked fibrin II is formed. From about 4 units to about 500 units of thrombin per ml of composition comprising noncrosslinked fibrin can be added or the thrombin can be provided by the desired site.

If the noncrosslinked fibrin has been solubilized, i.e., is a fibrin monomer, how the fibrin monomer is converted to fibrin polymer depends on how the solubilization was carried out, e.g., acid buffer or chaotropic agent. The formation of fibrin polymer can be carried out by the same methods as described above. This fibrin polymer, if desired, can then be converted to crosslinked fibrin by the addition of a source of calcium ions and activated factor XIII (or precursors to activated factor XIII) and, optionally, thrombin to the composition comprising fibrin monomer, as described above. The activated factor XIII can be added to the composition comprising noncrosslinked fibrin at a final concentration of from about 1.0 to about 20 units factor XIII per ml of composition comprising noncrosslinked fibrin. Alternatively, the factor XIII can be supplied by the blood or body fluids at the desired site or by the addition of autologous plasma to the composition comprising noncrosslinked fibrin. Nonlimiting sources of calcium ions include calcium chloride, preferably at a concentration of 30 mM. Alternatively, and less preferred, calcium ions can be supplied by the blood or body fluids at the desired site. From about 4 units to about 500 units of thrombin per ml. of composition comprising fibrin monomer can be added or the thrombin can be provided by the desired site.

FIBRIN SEALANT ADJUVANTS

The fibrin sealant of the subject invention can also contain adjuvants, for example, antibiotics, e.g., gentamycin, cefotaxim, nebacetin and sisomicin, histaminine $H_2$-antagonists, e.g., ranitidine, and anticancer drugs, e.g., OK-432. This can be carried out by adding the desired antibiotic to the composition comprising fibrin monomer or noncrosslinked fibrin. See M. C. H. Gersdorff and T. A. J. Robillard, *Laryngoscope*, 95:1278–80 (1985); A. Ederle et al., *Ital. J. Gastroenterol.*, 21:354–56 (1991); V. Ronfard et al., *Burns*, 17:181–84 (1991); T. Sakurai et al., *J. Control. Release*, 18:39–43 1992); T. Monden et al., *Cancer,* 69:636–42 (1992); F. Greco, *J. of Biomedical Materials Research*, 25:39–51 (1991) and H. B. Kram et al., *Journal of Surgical Research*, 50:175–178 (1991), the contents of which is incorporated herein by reference. Other adjuvants can also be added, for example, fibronectin, fibrinolytic inhibitors such as aprotinin, alpha-2 antiplasmin, PAI-1, PAI-2, 6-aminohexanoic acid, 4-aminomethyl cyclohexanoic acid, collagen or keratinocytes. It is believed that the dosage of such adjuvant is the same as that utilized in conventional fibrin sealants.

FIBRIN SEALANT KITS

The subject invention also provides fibrin sealant kits. The kit can contain as a first component a composition comprising fibrin monomer and a second component an alkaline buffer that is capable of polymerizing the fibrin monomer or distilled water, depending on how the solubilization step was performed. The second component can optionally contain a source of calcium ions. Alternatively, the first component can be a composition comprising noncrosslinked fibrin and the second component can be a source of calcium ions. If the source of fibrinogen utilized to prepare a composition comprising noncrosslinked fibrin is from cell cultures that secrete fibrinogen or recombinant fibrinogen, the first component can be a composition comprising noncrosslinked fibrin, the second component can be a source of calcium ions and a third component is activated factor XIII.

EXAMPLES

PLASMA PREPARATION FROM WHOLE BLOOD

Whole blood (100 ml) is collected into standard commercially available blood bag containing an anticoagulant such as citrate/phosphate/dextrose. The blood is then transferred to a container suitable for centrifugation and centrifuged at room temperature for 10 minutes at 3,000 g. The clear supernatant plasma (approximately 50 ml) is decanted and the cellular components are discarded.

An alternative method of plasma preparation from whole blood is by filtration. Again, 100 ml whole blood is collected into a bag containing a suitable anticoagulant such as citrate/phosphate/ dextrose. The blood is then recirculated over a filter exhibiting good protein transmission by means of peristaltic pump. The pressure drop across the membrane results in plasma being forced through with cellular components remaining in the recirculating blood. Plasma (50 ml) is collected for further processing.

IMMOBILIZATION OF BATROXOBIN ONTO BEADED AGAROSE

Beaded agarose (Pharmacia) was employed in immobilization studies. The agarose used was 4% crosslinked, 45–165 μm (90% of particles). This material swells to 5 times its volume when hydrated. Batroxobin is first oxidized with 0.1M sodium periodate for 1 hour at room temperature in a covered scintillation vial. The batroxobin is purified by passing through a sephadex® PD-10 gel permeation column. The oxidized batroxobin is then coupled to a hydrazide activation agarose gel overnight at room temperature in 50 mM sodium acetate pH 5.5 plus 10 mM sodium borohydride (30–200U per 1.75 g moist gel). The non-bound reactions are removed from the gel by washing with: ~50 ml mM sodium acetate pH 5.5, 100 ml 50 mM glycine/1M sodium chloride pH 3.0, 100 ml 50 mM sodium carbonate/1M sodium chloride 10.0, 100 ml 50 mM sodium phosphate/1M sodium chloride pH 7.0, 100 ml water, 100 ml 50 mM sodium phosphate/1M sodium chloride pH 7.0, 100 ml 50 mM sodium phosphate pH 7.0.

REACTION OF IMMOBILIZED ENZYME WITH PLASMA FIBRINOGEN TO FORM A COMPOSITION COMPRISING NONCROSSLINKED FIBRIN

The immobilized enzyme (350 mg) is added to approximately 50 ml of centrifuged or filtered plasma and gently mixed for 7 to 20 minutes until a non-crosslinked fibrin I polymer clot is formed.

The fibrin I polymer plus associated immobilized enzyme is then harvested by either: a) centrifugation at 3,000 g for 10 minutes followed by removal of the supernatant serum by decantation, or b) filtration through a suitable low protein binding filter followed by discarding the filtered serum and retaining the fibrin I polymer plus immobilised enzyme for further treatment. This fibrin I polymer is an example of a composition comprising noncrosslinked fibrin.

SOLUBILIZATION OF THE FIBRIN I POLYMER TO FORM A COMPOSITION COMPRISING FIBRIN MONOMER

Solubilization of the fibrin I polymer is achieved by the addition of about 1–4 ml of 0.2M sodium acetate pH 4.0 containing 30 mM calcium chloride buffer to the harvested fibrin I polymer plus immobilized enzyme. The sample is subsequently agitated vigorously, e.g., on a vortex mixer, for 2 minutes. Removal of the immobilized enzyme can then be achieved by filtration of the fibrin I solution through a 1 to 20 μm low protein binding filter. The agarose enzyme will be retained by the filter, thus allowing its removal from the system. The remaining solution, a composition comprising fibrin I monomer, consists of a concentrated acidic fibrin I monomer solution in conjunction with other plasma proteins. Generally, about 100 ml. of whole blood results in about 4 ml or 5 ml of the composition comprising fibrin monomer wherein the concentration of fibrin monomer is from about 25 mg/ml to about 35 mg/ml. This is now ready for delivery to the patient either, alone or, co-extruded with repolymerizing buffer to form a fibrin sealant.

REPOLYMERIZATION OF THE COMPOSITION COMPRISING FIBRIN I MONOMER

Repolymerization is achieved by simultaneous mixing of 9 parts of the solution comprising fibrin I monomer with 1 part of a suitable repolymerizing buffer, e.g., 0.75M sodium carbonate/sodium bicarbonate, pH 10.0. The ratio of mixing can be altered; however, a 9:1 ratio maintains the high concentration of fibrin in the final product. On co-extrusion the fibrin I spontaneously repolymerizes and converts to fibrin II followed by crosslinking of the fibrin over a period of about 30 minutes.

The present invention is not to be limited in scope by the specific embodiments described, which are intended as single illustrations of individual aspects of the invention. Indeed, various modifications of the subject invention in addition to those shown and described herein will become apparent to those skilled in the art from the foregoing description. Such modifications are intended to fall within the scope of the appended claims.

HYDRAZIDE ACTIVATION OF AGAROSE AND COUPLING VIA THE CARBOHYDRATE MOIETY OF THE ENZYME

In order to react the carbohydrate moiety of batroxobin with a hydrazide activated support, the sugar must first be oxidized to give free —CHO groups. This is accomplished as follows.

Batroxobin 1–7 mg is dissolved in 2 ml of water and 0.2 ml O.1M sodium periodate. The mixture is incubated at room temperature for 1 hour after which it is desalted on a Sephadex® G-25 gel filtration column. The oxidized active batroxobin is eluted from the column with 0.9% w/v sodium chloride.

Standard commercially available hydrazide activated agarose (Bio-rad Laboratories Ltd UK) or any group with a terminal free amino group can be employed to directly couple free aldehyde groups (—CHO). If hydrazide-agarose is used the coupling procedure is as follows.

1–5 g Hydrazide-agarose gel is suspended in 4 ml 50 mM sodium acetate pH 5.5. To the suspension is added 1 ml 10 mM sodium borohydride together with the desired amount of oxidized batroxobin (typically 100–200 BU per g moist gel).

The sample is mixed overnight at room temperature and subsequently washed on a sintered glass funnel with 50 ml 50 mM sodium acetate pH 5.5, 100 ml 50 mM glycine/1M sodium chloride pH 3.0, 100 ml 50 mM sodium carbonate/1M sodium chloride pH 10.0, 100 ml 50 mM sodium phosphate/1M sodium chloride pH 7.0, 100 ml water and 100 ml 50 mM sodium phosphate/1M sodium chloride pH 7.0 and finally 100 ml 50 mM sodium phosphate pH 7.0.

The method for reaction of the immobilised batroxobin with plasma is as follows.

The pH of plasma (50 ml) is reduced to pH 5.5 by the addition of acetic acid. To the plasma is added the equivalent of 100–200 BU of batroxobin immobilized to approximately 1.75 g (moist gel weight) agarose. The plasma is incubated at 37° C. for 10–15 minutes after which time the pH is increased to pH 7.4 by the addition of sodium hydroxide. Fibrin I polymerisation occurs almost instantaneously. The fibrin I polymer is harvested by centrifugation at 3,500 rpm for 10 minutes and redissolved in 3–4 ml of 0.2M sodium acetate pH 4.0 containing 30 mM calcium chloride. Agarose-enzyme can then be separated from fibrin I by centrifugation or filtration. The fibrin I is subsequently repolymerized to form the fibrin sealant by the addition of 9 parts fibrin I solution to 1 part 0.75M sodium carbonate/bicarbonate pH 10.0.

THE ENZYME CAPTURE SYSTEM USING BIOTIN-AVIDIN

Enzyme capture is performed by first biotinylating the batroxobin and capturing the biotin-enzyme with immobilized avidin (avidin-coupled to 6% crosslinked agarose).

Biotinylation of proteins can be achieved using a number of reagents. In this instance, N-hydroxysuccinimide-biotin (water insoluble) is used (commercially available from Amersham). NHS-biotin (50 μl) was added to 1 mg of batroxobin at pH 8.6 and the solution is incubated at room temperature for 1 hour. Excess biotinylation reagent is removed by gel filtration on a Sephadex® G-25 column with 0.1M potassium phosphate pH 7.5 as the eluent.

The equivalent of 10BU (biotin-batroxobin is added to 50 ml plasma and incubated at 37° C. for 10 minutes. Fibrin I polymer is harvested by centrifugation (3,500 rpm for 10 minutes) and redissolved in 3–4 ml of 0.2M sodium acetate pH 4.0 containing 30 mM calcium chloride. To the fibrin I, is added avidin-agarose (commercially available from Sigma Chemical Co.) at 0.2 g (moist gel) per ml fibrin I. The sample is incubated at room temperature for 10 minutes and centrifuged at 2,000 rpm for 10 minutes. The fibrin I produced is substantially free from batroxobin. Fibrin repolymerization to form the fibrin sealant is achieved as described in Example 5.6.

What is claimed is:

1. A method of applying a fibrin sealant comprising a fibrin polymer to a mammal in need thereof, which method comprises
    a) preparing a fibrin polymer by subjecting autologous fibrinogen to an enzyme which catalyzes the cleavage of fibrinopeptide A and/or B from fibrinogen, removing substantially all of the enzyme and
    b) applying the resulting fibrin sealant to said mammal.

2. A fribrin sealant comprising a fibrin polymer prepared by the steps of
    a) subjecting autologous fibrinogen to an enzyme which catalyzes the cleavage of fibrinopeptide A and/or B from fibrinogen, and
    b) removing substantially all of the enzyme to obtain the sealant.

* * * * *